US012370288B1

United States Patent
Hossain et al.

(10) Patent No.: US 12,370,288 B1
(45) Date of Patent: Jul. 29, 2025

(54) BIOBASED WOUND HEALING PREPARATION AND METHOD OF PREPARATION THEREOF

(71) Applicant: IMAM MOHAMMAD IBN SAUD ISLAMIC UNIVERSITY, Riyadh (SA)

(72) Inventors: Abm Sharif Hossain, Riyadh (SA); Hasan Ahmed Rudayni, Riyadh (SA); Mohammad Saad Aleissa, Riyadh (SA); Lina Mohammed Ateeq Alneghery, Riyadh (SA); Sulaiman Abdullah Ali Alsalameh, Riyadh (SA); Moniruddin Chowdhury, Kuala Lumpur (MY); Fazliny Abdul Rahman, Kuala Lumpur (MY)

(73) Assignee: IMAM MOHAMMAD IBN SAUD ISLAMIC UNIVERSITY, Riyadh (SA)

( * ) Notice: Subject to any disclaimer, the term of this patent is extended or adjusted under 35 U.S.C. 154(b) by 0 days.

(21) Appl. No.: 19/042,975

(22) Filed: Jan. 31, 2025

(51) Int. Cl.
*A61L 26/00* (2006.01)
*C08L 1/02* (2006.01)
*C08L 3/02* (2006.01)
*B82Y 5/00* (2011.01)

(52) U.S. Cl.
CPC ....... *A61L 26/0057* (2013.01); *A61L 26/0004* (2013.01); *A61L 26/0052* (2013.01); *C08L 1/02* (2013.01); *C08L 3/02* (2013.01); *A61L 2300/30* (2013.01); *A61L 2400/12* (2013.01); *A61L 2430/34* (2013.01); *B82Y 5/00* (2013.01)

(58) Field of Classification Search
CPC .................................................. A61L 26/0057
See application file for complete search history.

(56) References Cited

U.S. PATENT DOCUMENTS

| 2017/0258739 A1 | 9/2017 | Busse et al. |
| 2019/0225651 A1 | 7/2019 | Zouani |
| 2021/0361741 A1 | 11/2021 | Grek et al. |

OTHER PUBLICATIONS

Al-Ghanayem et al., Moringa Oleifera Extract Promotes Healing of Infected Wounds in Diabetic Rats: Evidence of Antimicrobial, Antioxidant and Proliferative Proliferative, Pharmaceuticals, 15, 528. (Year: 2022).*

Farnaz Jaberifard, et al., "A novel insoluble film based on crosslinked-starch with gelatin containing ZnO-loaded halloysite nanotube and bacterial nanocellulose for wound healing applications", Applied Clay Science, vol. 230, Nov. 15, 2022 (9 pages).

(Continued)

*Primary Examiner* — Carlos A Azpuru
(74) *Attorney, Agent, or Firm* — Oblon, McClelland, Maier & Neustadt, L.L.P.

(57) ABSTRACT

A biobased wound healing preparation including a nanocomposite including olive leaf extract, beef bone meal, and moringa seed gel, an organic composition including one or more of a beetroot dye, black cumin seed, sodium fusidate, salicylic acid, chicken-sourced glycerin, and pomegranate peel pigment, an adhesive component including one or more of a cyanoacrylate, *Acacia nilotica* glue, coconut gel, okra gel, aloe vera gel, and aroid root gum, and ZnO nanoparticles. The nanocomposite is in the form of nanoparticles having an average particle size of 25 nm or less.

19 Claims, 9 Drawing Sheets

(56) References Cited

OTHER PUBLICATIONS

Mehran Alavi, et al., "An overview on antimicrobial and wound healing properties of ZnO nanobiofilms, hydrogels, and bionanocomposites based on cellulose, chitosan, and alginate polymers", Carbohydrate Polymers, Jan. 1, 2020. 115349 (7 pages).

* cited by examiner

BIOBASED WOUND HEALING PREPARATION AND METHOD OF PREPARATION THEREOF

BACKGROUND

Technical Field

The present disclosure is directed towards wound healing preparations, more particularly, a biobased wound healing preparation and a method of preparing the biobased wound healing preparation.

Description of Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly nor impliedly admitted as prior art against the present invention.

Wound healing refers to a living organism's ability to replace destroyed or damaged cells or tissues with newly produced tissues using different materials and substances. In humans, there are four main stages of wound healing including: hemostasis, inflammation, proliferation, and remodeling. Hemostasis involves the formation of a blood clot at the site of the injury to stop bleeding. After injury, the damaged cells release proteins that attract immune cells, such as white blood cells, to the area resulting in inflammation. Inflammation may make the skin appear red and swollen. Proliferation, or the granulation stage, occurs when new tissue and blood vessels develop in a wound. During this stage, the wound appears red or pink, bumpy, moist, and raised above the surrounding skin. The bumpy appearance is caused by new capillary loops that develop to supply oxygen and nutrients to the new tissue. The remodeling stage, also called the maturation stage, is the final stage of wound healing where newly formed tissue is refined and strengthened, essentially creating a scar by reorganizing collagen fibers and contracting the wound to achieve maximum tensile strength. Depending on the severity of the injury, the remodeling stage can last for days to weeks after the initial injury.

Traditional wound healing preparations comprise different types of chemicals such as bacitracin, silver, iodine, chlorhexidine, hydrogen peroxide, and potassium permanganate which may cause allergic reactions, antibiotic resistance, toxicity if absorbed into the bloodstream through an open wound, local and/or systemic toxic effects, and contact dermatitis. Therefore, one objective of this disclosure is to develop a wound-healing material developed from biological sources for medical use that is biodegradable, organic, and biologically inert allowing for increased compatibility with human skin without impacting the environment.

SUMMARY

In an exemplary embodiment, a biobased wound healing preparation is described. The biobased wound healing preparation comprises a nanocomposite comprising olive leaf extract, beef bone meal, and moringa seed gel; an organic composition comprising at least one selected from the group consisting of a beetroot dye, black cumin seed, sodium fusidate, salicylic acid, chicken-sourced glycerin, and pomegranate peel pigment; an adhesive component comprising at least one of a cyanoacrylate, *Acacia nilotica* glue, coconut gel, okra gel, aloe vera gel, and aroid root gum; and ZnO nanoparticles. The nanocomposite is in the form of nanoparticles having an average particle size of 25 nm or less.

In some embodiments, the organic composition comprises 1 to 5 wt. % of at least one selected from the group consisting of fusidic acid and salicylic acid relative to a total weight of the organic composition.

In some embodiments, the biobased wound healing preparation comprises ZnO nanoparticles in an amount of 1 to 10 wt. % relative to a total weight of the biobased wound healing preparation.

In some embodiments, the nanocomposite is a cellulose composition comprising 25 to 50 wt. % of a nanocellulose relative to a total weight of the nanocomposite.

In some embodiments, the nanocomposite is a starch composition comprising 20 to 40 wt. % of a nanostarch relative to a total weight of the nanocomposite In some embodiments, the biobased wound healing preparation achieves a wound healing time of less than 10 days as compared to a synthetic polymer wound healing preparation.

In some embodiments, the nanocomposite is in the form of nanoparticles having an average particle size of 15 nm or less.

In some embodiments, the biobased wound healing preparation comprises ZnO nanoparticles in an amount of 1 to 5 wt. % relative to a total weight of the biobased wound healing preparation.

In some embodiments, the biobased wound healing preparation achieves a wound healing time of less than 8 days as compared to a synthetic polymer wound healing preparation.

In some embodiments, the biobased wound healing preparation comprises the nanocomposite in an amount of 35 to 55 wt. % relative to a total weight of the biobased wound healing preparation.

In some embodiments, the ZnO nanoparticles are spherical and have an average particle size of 40 nm or less.

In some embodiments, the biobased wound healing preparation has a pH of 5 to 8.

In an exemplary embodiment, a method of producing the biobased wound healing preparation is described. The method comprises hydrolyzing a mixture of olive leaf extract, beef bone meal, and moringa seed gel with at least one inorganic acid to obtain the nanocomposite; preparing ZnO nanoparticles; and combining the nanocomposite with the organic composition, ZnO nanoparticles, and the adhesive component to form the biobased wound healing preparation.

In some embodiments, the method further comprises drying the olive leaf extract, beef bone meal, and moringa seed gel at a temperature of 100 to 150° C. for 1 to 5 h to obtain the mixture of olive leaf extract, beef bone meal, and moringa seed gel.

In some embodiments, the inorganic acid is selected from the group consisting of hydrochloric acid, sulfuric acid, nitric acid, phosphoric acid, hydrofluoric acid, formic acid, and trifluoroacetic acid.

In some embodiments, the method of preparing ZnO nanoparticles comprises reacting a zinc precursor with an organic solvent to obtain a reaction mixture, sonicating the reaction mixture then heating the reaction mixture for 12 to 36 h to obtain a final suspension, and centrifuging the final suspension to obtain the ZnO nanoparticles.

In some embodiments, the inorganic acid is selected from the group consisting of hydrochloric acid and sulfuric acid.

In some embodiments, the ZnO nanoparticles have an average particle size of 40 nm or less.

In some embodiments, the organic composition comprises beetroot dye in an amount of 5 to 15 wt. % relative to a total weight of the organic composition.

In some embodiments, the organic composition comprises pomegranate peel pigment in an amount of 5 to 15 wt. % relative to a total weight of the organic composition.

The foregoing general description of the illustrative embodiments and the following detailed description thereof are merely exemplary aspects of the teachings of this disclosure and are not restrictive.

BRIEF DESCRIPTION OF THE DRAWINGS

A more complete appreciation of this disclosure and many of the attendant advantages thereof will be readily obtained as the same becomes better understood by reference to the following detailed description when considered in connection with the accompanying drawings, wherein.

DETAILED DESCRIPTION

In the drawings, like reference numerals designate identical or corresponding parts throughout the several views. Further, as used herein, the words "a", "an" and the like generally carry a meaning of "one or more", unless stated otherwise.

Furthermore, the terms "approximately," "approximate", "about" and similar terms generally refer to ranges that include the identified value within a margin of 20%, 10%, or preferably 5%, and any values therebetween.

As used herein, "particle size" may be considered the lengths or longest dimensions of a particle.

As used herein, the term "polymer" refers to a large molecule comprising a chain of smaller repeating units called monomers.

A weight percent of a component, unless specifically stated to the contrary, is based on the total weight of the formulation or composition in which the component is included. For example, if a particular element or component in a composition or article is said to have 5 wt. %, it is understood that this percentage is in relation to a total compositional percentage of 100 wt. %.

According to a first aspect of the present disclosure, a biobased wound healing preparation is described. The biobased wound healing preparation comprises a nanocomposite comprising olive leaf extract, beef bone meal, and moringa seed gel, an organic composition comprising at least one selected from the group consisting of a beetroot dye, black cumin seed, sodium fusidate, salicylic acid, chicken-sourced glycerin, and pomegranate peel pigment, an adhesive component comprising at least one of a cyanoacrylate, *Acacia nilotica* glue, coconut gel, okra gel, aloe vera gel, and aroid root gum, and ZnO nanoparticles.

The nanocomposite is preferably obtained from biobased materials. Biobased materials include naturally occurring, renewable sources and may be of plant or animal origin. In a specific embodiment, the nanocomposite comprises olive leaf extract, beef bone meal, and moringa seed gel. In an embodiment, the nanocomposite comprises olive leaf extract. Olive leaf extract may aid in wound healing due to its anti-inflammatory and antimicrobial properties. Further, olive leaf extract may help repair epithelial tissues due to its high collagen content. In some embodiments, the nanocomposite comprises 1 to 5 wt. % of olive leaf extract relative to a total weight of the nanocomposite, preferably 1 to 4.5 wt. %, preferably 1 to 4 wt. %, preferably 1 to 3.5 wt. %, preferably 1 to 3 wt. %, preferably 1 to 2.5 wt. %, preferably 1 to 2 wt. %, preferably 1 to 1.5 wt. %, most preferably 1 wt. % relative to a total weight of the nanocomposite. In an embodiment, the nanocomposite comprises beef bone meal. Beef bone meal may be used as a source of calcium, phosphorus, and other trace elements such as zinc, copper, and iron. Calcium, phosphorus, and trace elements like zinc, copper, and iron play a crucial role in wound healing by supporting various stages of the process, including blood clotting, cell proliferation, collagen synthesis, and tissue remodeling, essentially contributing to the structural integrity of the newly formed tissue at the wound site. Calcium and phosphorus may combine to form hydroxyapatite, a mineral component of the extracellular matrix which provides structural support for the newly forming tissue during wound healing. Calcium ions may also aid in signaling pathways, helping to regulate various cellular processes like cell migration, adhesion, and proliferation. Zinc may play role in cell division, collagen synthesis, and immune function, to aid in wound healing. Iron is important for oxygen delivery to the wound site, supporting cell proliferation and tissue repair which further aids wound healing. In some embodiments, the nanocomposite comprises 2 to 6 wt. % of beef bone extract relative to a total weight of the nanocomposite, preferably 2 to 5.5 wt. %, preferably 2 to 5 wt. %, preferably 2 to 4.5 wt. %, preferably 2 to 4 wt. %, preferably 2 to 3.5 wt. %, preferably 2 to 3 wt. %, preferably 2 to 2.5 wt. %, most preferably 2 wt. % relative to a total weight of the nanocomposite. In some embodiments, the nanocomposite comprises moringa seed gel. Moringa is a plant native to India, having antifungal, antiviral, and anti-inflammatory properties. Further, moringa seed gel may aid in wound healing by protecting skin keratinocytes from oxidative stress injuries. In an embodiment, the nanocomposite comprises 3 to 10 wt. % of moringa seed gel relative to a total weight of the nanocomposite, preferably 3 to 9.5 wt. %, preferably 3.5 to 9 wt. %, preferably 4 to 8.5 wt. %, preferably 4 to 8 wt. %, preferably 4 to 7.5 wt. %, preferably 4 to 7 wt. %, preferably 4 to 6.5 wt. %, preferably 4 to 6 wt. %, preferably 4 to 5.5 wt. %, preferably 4 to 5 wt. %, preferably 4 to 4.5 wt. %, most preferably 4 wt. % relative to a total weight of the nanocomposite. In one embodiment, the nanocomposite is present in an amount of 35 to 55 wt. % relative to a total weight of the biobased wound healing preparation, preferably 36 to 54 wt. %, preferably 37 to 53 wt. %, preferably 38 to 52 wt. %, preferably 39 to 51 wt. %, preferably 40 to 50 wt. %, preferably 41 to 49 wt. %, preferably 42 to 48 wt. %, preferably 43 to 47 wt. %, preferably 44 to 46 wt. %, most preferably 45 wt. % relative to a total weight of the biobased wound healing preparation.

In an embodiment, the nanocomposite is a cellulose composition comprising 25 to 50 wt. % of a nanocellulose derived from the olive leaf extract, beef bone meal, and moringa seed gel relative to the total weight of the nanocomposite. In some embodiments, the nanocomposite is a cellulose composition comprising 26 to 49 wt. % of a nanocellulose, preferably 27 to 48 wt. %, preferably 28 to 47 wt. %, preferably 29 to 46 wt. %, preferably 30 to 45 wt. %, preferably 31 to 44 wt. %, preferably 32 to 43 wt. %, preferably 33 to 42 wt. %, preferably 34 to 41 wt. %, preferably 35 to 40 wt. %, preferably 36 to 39 wt. %, preferably 37 to 39 wt. %, preferably 38 to 39 wt. %. In a specific embodiment, the nanocomposite is a cellulose composition comprising 38.3±0.1 wt. % of a nanocellulose derived from the olive leaf extract, beef bone meal, and moringa seed gel relative to a total weight of the nanocomposite. In some embodiments, the nanocellulose has an average particle size of 22 nm or less, preferably 21.5 nm or less, preferably 21 nm or less, preferably 20.5 nm or less, preferably 20 nm or less, preferably 19.5 nm or less, preferably 19 nm or less, preferably 18.5 nm or less, preferably 18 nm or less, preferably 17.5 nm or less, preferably 17 nm or less, preferably 16.5 nm or less, most preferably 16 nm or less.

In another embodiment, the nanocomposite is a starch composition comprising 20 to 40 wt. % of a nanostarch derived from the olive leaf extract, beef bone meal, and moringa seed gel relative to a total weight of the nanocomposite. In some embodiments, the nanocomposite is a starch composition comprising 21 to 39 wt. % of a nanostarch, preferably 22 to 38 wt. %, preferably 23 to 37 wt. %, preferably 24 to 36 wt. %, preferably 25 to 35 wt. %, preferably 26 to 34 wt. %, preferably 27 to 33 wt. %, preferably 28 to 32 wt. %, preferably 29 to 31 wt. %, preferably 30 wt. %. In a specific embodiment, the nanocomposite is a starch composition comprising 30.0±0.1 wt. % of a nanostarch derived from the olive leaf extract, beef bone meal, and moringa seed gel relative to the total weight of the biobased wound healing preparation. In some embodiments, the nanostarch has an average particle size of 20 nm or less, preferably 19.5 nm or less, preferably 19 nm or less, preferably 18.5 nm or less, preferably 18 nm or less, preferably 17.5 nm or less, preferably 17 nm or less, preferably 16.5 nm or less, preferably 16 nm or less, preferably 15.5 nm or less, preferably 15 nm or less, preferably 14.5 nm or less, most preferably 14 nm or less.

In an embodiment, the organic composition comprises at least one selected from the group consisting of a beetroot dye, black cumin seed, sodium fusidate, salicylic acid, chicken-sourced glycerin, and pomegranate peel pigment. In one embodiment, the organic composition comprises fusidic acid, its salt, its derivatives, or mixtures thereof (e.g., sodium fusidate, potassium fusidate, fusidic acid esters, fusidic acid amidates, fusidic acid complexes). Fusidic acid is an antibiotic that treats bacterial infections, including skin and eye infections, due to its activity against common skin pathogens such as *Staphylococcus aureus*. In an embodiment, fusidic acid is present in an amount of 1 to 5 wt. % relative to a total weight of the organic composition, preferably 1 to 4.5 wt. %, preferably 1 to 4 wt. %, preferably 1 to 3.5 wt. %, preferably 1 to 3 wt. %, preferably 1 to 2.5 wt. %, preferably 1 to 2 wt. %, preferably 1 to 1.5 wt. %, most preferably 1 wt. % relative to a total weight of the organic composition. In another embodiment, the organic composition comprises salicylic acid, its salt, its derivatives, or mixtures thereof. Salicylic acid is an anti-inflammatory exfoliant that promotes skin renewal by inducing epithelial actin reorganization through activation of the AMP-activated protein kinase. In an embodiment, salicylic acid is present in an amount of 1 to 5 wt. % relative to a total weight of the organic composition, preferably 1 to 4.5 wt. %, preferably 1 to 4 wt. %, preferably 1 to 3.5 wt. %, preferably 1 to 3 wt. %, preferably 1 to 2.5 wt. %, preferably 1 to 2 wt. %, preferably 1 to 1.5 wt. %, most preferably 1 wt. % relative to a total weight of the organic composition.

In one embodiment, the organic composition comprises black cumin seed. *Nigella sativa* (also known as black cumin) is an annual flowering plant in the family Ranunculaceae, native to eastern Europe. Black cumin seed may promote with wound healing due to its antibacterial, anti-inflammatory, and antioxidant properties. Moreover, black cumin seed contains thymoquinone which may stimulate tissue growth and increase collagen production. In an embodiment, the black cumin seed is present in an amount of 1 to 5 wt. % relative to a total weight of the organic composition, preferably 1.5 to 4.5 wt. %, preferably 2 to 4 wt. %, preferably 2 to 3.5 wt. %, preferably 2 to 3 wt. %, preferably 2 to 2.5 wt. %, most preferably 2 wt. % relative to a total weight of the organic composition.

In some embodiments, the organic composition comprises an animal-sourced glycerin. Glycerin may be obtained from animal fat. Glycerin may aid in wound healing by creating an environment that reduces the number of microbes in the wound due to it acting as a protective layer for destroyed mucous membranes. Further, glycerin is a natural humectant with a high osmotic pressure and binding force allowing it to exist outside a wound without penetrating the tissue. This may help exudates, viruses, and contaminants to exit the wound, which aids in cleaning the wound and ultimately promoting healing of the wound. In some embodiments, the organic composition comprises glycerin derived from chicken legs or chicken toes. In an embodiment, the glycerin is present in an amount of 1 to 15 wt. % relative to a total weight of the organic composition, preferably 2 to 14 wt. %, preferably 3 to 13 wt. %, preferably 4 to 12 wt. %, preferably 5 to 11 wt. %, preferably 5 to 10 wt. %, preferably 5 to 9 wt. %, preferably 5 to 8 wt. %, preferably 5 to 7 wt. %, preferably 5 to 6 wt. %, most preferably 5 wt. % relative to a total weight of the organic composition.

In some embodiments, the organic composition comprises at least one organic dye. In another embodiment, the organic dye is obtained from at least one selected from the group consisting of beetroot peel and pomegranate peel. Beetroot peel may aid in wound healing by increasing the rate of wound contraction and decreasing the time it takes for wounds to fully epithelialize. Beetroot peel extract may also have antimicrobial activity against gram-positive bacteria, gram-negative bacteria, and some fungus, aiding in wound healing by decreasing the risk of infection. In an embodiment, the organic composition comprises beetroot peel dye and pomegranate peel dye. In some embodiments, the beetroot peel dye and pomegranate peel dye are present in the organic composition in an amount of 10 to 30 wt. % relative to a total weight of the organic composition, preferably 11 to 29 wt. %, preferably 12 to 28 wt. %, preferably 13 to 27 wt. %, preferably 14 to 26 wt. %, preferably 14 to 25 wt. %, preferably 14 to 24 wt. %, preferably 14 to 23 wt. %, preferably 14 to 22 wt. %, preferably 14 to 21 wt. %, preferably 14 to 20 wt. %, preferably 14 to 19 wt. %, preferably 14 to 18 wt. %, preferably 14 to 17 wt. %, preferably 14 to 16 wt. %, preferably 14 to 15 wt. %, most preferably 14 wt. % relative to a total weight of the organic composition. In some embodiments, the organic composition comprises a beetroot dye in an amount of 5 to 15 wt. % relative to a total weight of the organic composition, preferably 6 to 14 wt. %, preferably 7 to 13 wt. %, preferably 7 to 12 wt. %, preferably 7 to 11 wt. %, preferably 7 to 10 wt. %, preferably 7 to 9 wt. %, preferably 7 to 8 wt. %, most preferably 7 wt. % relative to a total weight of the organic composition. In some embodiments, the organic composition comprises pomegranate peel dye in an amount of 5 to 15 wt. % relative to a total weight of the organic composition, preferably 6 to 14 wt. %, preferably 7 to 13 wt. %, preferably 7 to 12 wt. %, preferably 7 to 11 wt. %, preferably 7 to 10 wt. %, preferably 7 to 9 wt. %, preferably 7 to 8 wt. %, most preferably about 7 wt. % relative to a total weight of the organic composition.

In one embodiment, the biobased wound healing preparation comprises 15 to 30 wt. % of the organic composition relative to a total weight of the biobased wound healing preparation, preferably 16 to 29 wt. %, preferably 17 to 28 wt. %, preferably 18 to 27 wt. %, preferably 19 to 26 wt. %, preferably 20 to 26 wt. %, preferably 21 to 26 wt. %, preferably 22 to 26 wt. %, preferably 23 to 26 wt. %, preferably 24 to 26 wt. %, preferably 25 to 26 wt. %, most preferably 26 wt. % relative to a total weight of the biobased wound healing preparation.

The biobased wound healing preparation further comprises an adhesive component comprising at least one of a cyanoacrylate, *Acacia nilotica* glue, coconut gel, okra gel, aloe vera gel, and aroid root gum. Cyanoacrylates may aid in wound healing by functioning as a waterproof occlusive dressing, thus maintaining a moist environment, enhancing epidermal migration, promoting angiogenesis, and increasing connective tissue synthesis. Cyanoacrylates may also have antimicrobial properties against gram-positive organisms, decreasing the risk of infection. In some embodiments, the cyanoacrylate is present in an amount of 1 to 10 wt. % relative to a total weight of the adhesive component, preferably 1.5 to 9.5 wt. %, preferably 2 to 9 wt. %, preferably 2 to 8.5 wt. %, preferably 2 to 8 wt. %, preferably 2 to 7.5 wt. %, preferably 2 to 7 wt. %, preferably 2 to 6.5 wt. %, preferably 2 to 6 wt. %, preferably 2 to 5.5 wt. %, preferably 2 to 5 wt. %, preferably 2 to 4.5 wt. %, preferably 2 to 4 wt. %, preferably 2 to 3.5 wt. %, preferably 2 to 3 wt. %, preferably 2 to 2.5 wt. %, most preferably 2 wt. % relative to a total weight of the adhesive component. Suitable examples of the cyanoacrylate polymers include, but are not limited to, methyl cyanoacrylate (MCA), ethyl cyanoacrylate (ECA), butyl cyanoacrylate (BCA), octyl cyanoacrylate (OCA), 2-cyanoacryloxyethyl acrylate, alkoxy ethyl cyanoacrylate, methoxypropyl cyanoacrylate, and the like.

In some embodiments, the adhesive component comprises *Acacia nilotica* glue. In some embodiments, the organic composition comprises *Acacia nilotica* glue. *Acacia nilotica* (Babul tree) is a gum-yielding *Acacia* species found in the Indian subcontinent. *Acacia nilotica* glue may aid in wound healing by increasing angiogenesis, collagen deposition, epithelization, and wound contraction. Moreover, *Acacia nilotica* glue has antimicrobial, antioxidant, and anti-inflammatory properties, making it a suitable additive to wound healing preparations. In an embodiment, the *Acacia nilotica* glue is present in an amount of 1 to 10 wt. % relative to a total weight of the adhesive component, preferably 1.5 to 9.5 wt. %, preferably 2 to 8 wt. %, preferably 2.5 to 8.5 wt. %, preferably 3 to 8 wt. %, preferably 3 to 7.5 wt. %, preferably 3 to 7 wt. %, preferably 3 to 6.5 wt. %, preferably 3 to 6 wt. %, preferably 3 to 5.5 wt. %, preferably 3 to 5 wt. %, preferably 3 to 4.5 wt. %, preferably 3 to 4 wt. %, preferably 3 to 3.5 wt. %, most preferably 3 wt. % relative to a total weight of the adhesive component.

In an embodiment, the adhesive component comprises coconut gel. Coconut gel contains monolaurin, a fatty acid that helps prevent infection which, in turn, aids wound healing. Coconut gel may also aid wound healing due to its antioxidant and anti-inflammatory properties. Moreover, coconut gel may increase collagen levels and increase moisture at the wound site, further aiding wound healing. In one embodiment, the coconut gel is present in an amount of 1 to 10 wt. % relative to a total weight of the adhesive component, preferably 1.5 to 9.5 wt. %, preferably 2 to 9 wt. %, preferably 2 to 8.5 wt. %, preferably 2 to 8 wt. %, preferably 2 to 7.5 wt. %, preferably 2 to 7 wt. %, preferably 2 to 6.5 wt. %, preferably 2 to 6 wt. %, preferably about 2 to 5.5 wt. %, preferably 2 to 5 wt. %, preferably 2 to 4.5 wt. %, preferably 2 to 4 wt. %, preferably 2 to 3.5 wt. %, preferably 2 to 3 wt. %, preferably 2 to 2.5 wt. %, more preferably 2 wt. % relative to a total weight of the adhesive component.

In an embodiment, the adhesive component comprises okra gel. Okra is rich in vitamins, minerals, and phenolic compounds. The mucilage content in okra fruits may be used to form a natural gel. Okra gel may aid wound healing by promoting cell migration and enhancing pro-angiogenesis. Okra gel may also increase wound bed moisture while also allowing oxygen to permeate the wound site, increasing healing. In one embodiment, the okra gel is present in an amount of 1 to 10 wt. % relative to a total weight of the adhesive component, preferably 1.5 to 9.5 wt. %, preferably 2 to 9 wt. %, preferably 2.5 to 8.5 wt. %, preferably 3 to 8 wt. %, preferably 3 to 7.5 wt. %, preferably 3 to 7 wt. %, preferably 3 to 6.5 wt. %, preferably 3 to 6 wt. %, preferably 3 to 5.5 wt. %, preferably about 3 to 5 wt. %, preferably 3 to 4.5 wt. %, preferably 3 to 4 wt. %, preferably 3 to 3.5 wt. %, most preferably 3 wt. % relative to a total weight of the adhesive component.

In an embodiment, the adhesive component comprises aloe vera gel. Aloe vera gel may aid in wound healing by increasing the amount of collagen at the wound area. Aloe vera gel may also change the composition of collagen and increase collagen cross-linking, thus promoting wound healing. Aloe vera gel may also increase the flexibility and reduce the fragility of the skin due to the increased moisture content. In an embodiment, the aloe vera gel is present in an amount of 1 to 10 wt. % relative to a total weight of the adhesive component, preferably 1.5 to 9.5 wt. %, preferably 2 to 9 wt. %, preferably 2 to 8.5 wt. %, preferably 2 to 8 wt. %, preferably 2 to 7.5 wt. %, preferably about 2 to 7 wt. %, preferably 2 to 6.5 wt. %, preferably 2 to 6 wt. %, preferably 2 to 5.5 wt. %, preferably 2 to 5 wt. %, preferably 2 to 4.5 wt. %, preferably 2 to 4 wt. %, preferably 2 to 3.5 wt. %, preferably 2 to 3 wt. %, preferably 2 to 2.5 wt. %, most preferably 2 wt. % relative to a total weight of the adhesive component.

In an embodiment, the adhesive component comprises aroid root gum. Aroids are from the family Araceae and include many common houseplants like aglaonemas, monsteras, philodendrons, pothos and ZZ plants. Aroid root gum may increase wound healing by increasing vascular endothelial growth factor (VEGF), which improves fibroblast activity in the wound area. Moreover, aroid root gum may have antioxidant properties resulting in increased wound healing. In an embodiment, the aroid root gum is present in an amount of 1 to 10 wt. % relative to a total weight of the adhesive component, preferably 1.5 to 9.5 wt. %, preferably 2 to 9 wt. %, preferably 2 to 8.5 wt. %, preferably 2 to 8 wt. %, preferably 2 to 7.5 wt. %, preferably about 2 to 7 wt. %, preferably 2 to 6.5 wt. %, preferably 2 to 6 wt. %, preferably 2 to 5.5 wt. %, preferably 2 to 5 wt. %, preferably 2 to 4.5 wt. %, preferably 2 to 4 wt. %, preferably 2 to 3.5 wt. %, preferably 2 to 3 wt. %, preferably 2 to 2.5 wt. %, most preferably 2 wt. % relative to a total weight of the adhesive component.

In one embodiment, the biobased wound healing preparation comprises 15 to 30 wt. % of the adhesive component relative to a total weight of the biobased wound healing preparation, preferably 16 to 29 wt. %, preferably 17 to 28 wt. %, preferably 18 to 27 wt. %, preferably 19 to 27 wt. %, preferably 20 to 27 wt. %, preferably 21 to 27 wt. %, preferably 22 to 7 wt. %, preferably 23 to 27 wt. %, preferably 24 to 27 wt. %, preferably 25 to 27 wt. %, preferably 26 to 27 wt. %, most preferably 27 wt. % relative to a total weight of the biobased wound healing preparation.

In an embodiment, the biobased wound healing preparation comprises ZnO nanoparticles. ZnO nanoparticles have antimicrobial properties against a wide range of bacteria, fungi, and viruses. Further, ZnO nanoparticles have anti-inflammatory properties which may aid wound healing by reducing inflammation at the wound site. ZnO nanoparticles may also help reduce oxidative stress, increase tissue granulation, and stimulate cell migration at the wound site. The ZnO nanoparticles may exists in variety of morphological shapes, such as nanowires, nanospheres, nanocrystals, nanorectangles, nanotriangles, nanopentagons, nanohexagons, nanoprisms, nanodisks, nanocubes, nanoribbons, nanoblocks, nanotoroids, nanodiscs, nanobarrels, nanogranules, nanowhiskers, nanoflakes, nanofoils, nanopowders, nanoboxes, nanobeads, nanobelts, nano-urchins, nanoflowers, nanostars, tetrapods, etc., and mixtures thereof. In a preferred embodiment, the ZnO nanoparticles are spherical. In an embodiment, the ZnO nanoparticles have an average particle size of 40 nm or less, preferably 39 nm or less, preferably 38 nm or less, preferably 37 nm or less, preferably 36 nm or less, preferably 35 nm or less, preferably 34 nm or less, preferably 33 nm or less, preferably 32 nm or less, preferably 31 nm or less, preferably 30 nm or less, preferably 29 nm or less, preferably 28 nm or less, preferably 27 nm or less, preferably 26 nm or less, preferably 25 nm or less, preferably 24 nm or less, preferably 23 nm or less, preferably 22 nm or less, preferably 21 nm or less, most preferably 20 nm or less. In an embodiment, the biobased wound healing preparation comprises ZnO nanoparticles in an amount of 1 to 10 wt. % relative to a total weight of the biobased wound healing preparation, preferably 1.5 to 9.5 wt. %, preferably 2 to 9 wt. %, preferably 2 to 8.5 wt. %, preferably 2 to 8 wt. %, preferably 2 to 7.5 wt. %, preferably 2 to 7 wt. %, preferably 2 to 6.5 wt. %, preferably 2 to 6 wt. %, preferably 2 to 5.5 wt. %, preferably 2 to 5 wt. %, preferably 2 to 4.5 wt. %, preferably 2 to 4 wt. %, preferably 2 to 3.5 wt. %, preferably 2 to 3 wt. %, preferably 2 to 2.5 wt. %, most preferably 2 wt. % relative to the total weight of the biobased wound healing preparation.

In some embodiments, the nanocomposite is in the form of nanoparticles having an average particle size of 25 nm or less, preferably 24.5 nm or less, preferably 24 nm or less, preferably 23.5 nm or less, preferably 23 nm or less, preferably 22.5 nm or less, preferably 22 nm or less, preferably 21.5 nm or less, preferably 21 nm or less, preferably 20.5 nm or less, preferably 20 nm or less, preferably 19.5 nm or less, preferably 19 nm or less, preferably 18.5 nm or less, preferably 18 nm or less, preferably 17.5 nm or less, preferably 17 nm or less, preferably 16.5 nm or less, preferably 16 nm or less, preferably 15.5 nm or less, most preferably 15 nm or less. In some embodiments, the nanocomposite is mixed with at least one additive to form a liquid, gel, or semi-suspended bio-based wound healing preparation. Suitable additives may include natural solvents such as water, ethanol (grain alcohol), isopropanol (rubbing alcohol), glycerol (vegetable glycerin), acetone, and ethyl acetate and gelling agents such as agar, carrageenan, gelatin, pectin, sodium alginate, and xanthan gum. In another embodiment, the bio-based wound healing preparation is a semi-suspended solution comprising the nanocomposite having an average particle size of 25 nm or less, the organic composition, the adhesive component, and ZnO nanoparticles where at least one of the organic composition, the adhesive component, and the ZnO nanoparticles is in a liquid form. In some embodiments, the biobased wound healing preparation has a pH ranging from 5 to 8, preferably 5.5 to 7.5, preferably 6 to 7.5, preferably 6.5 to 7.5, preferably 7 to 7.5, most preferably 7.5. In an embodiment, the biobased wound healing preparation achieves a wound healing time of less than 10 days, preferably less than 9.5 days, preferably less than 9 days, preferably less than 8.5 days, preferably less than 8 days, as compared to a synthetic polymer wound healing preparation.

Figure 1:
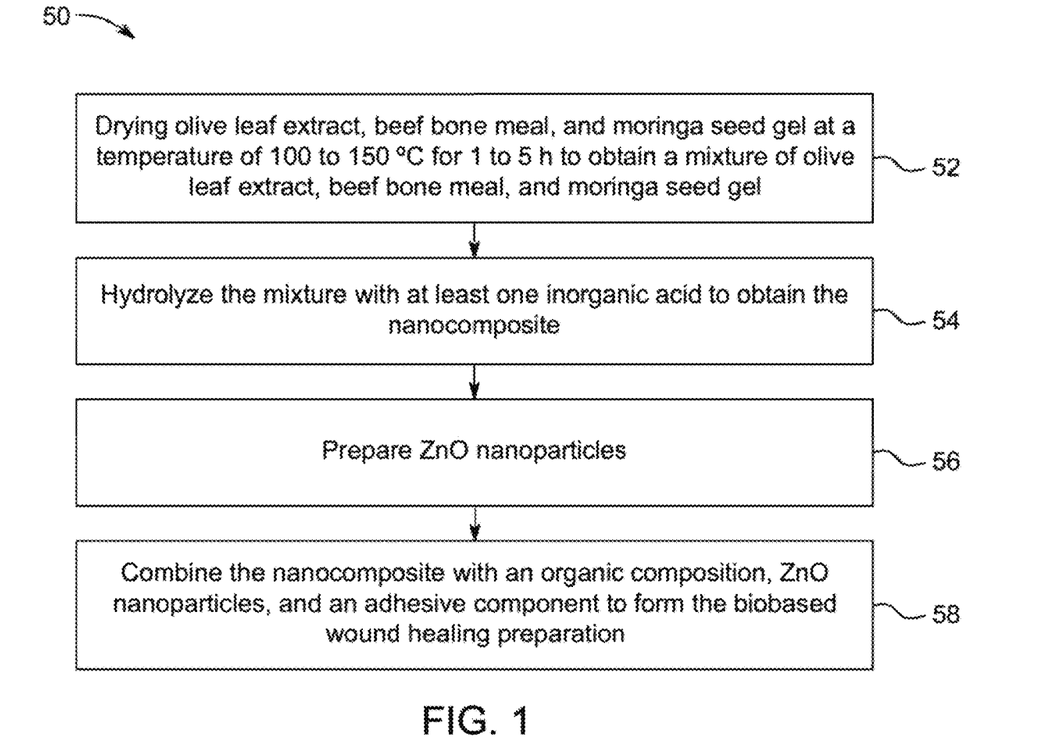
FIG. 1 is a flowchart depicting a method of preparing a biobased wound healing preparation, according to certain embodiments.

FIG. 1 illustrates a schematic flow chart of a method 50 of producing the biobased wound healing preparation. The order in which the method 50 is described is not intended to be construed as a limitation, and any number of the described method steps can be combined to implement the method 50. Additionally, individual steps may be removed or skipped from the method 50 without departing from the spirit and scope of the present disclosure.

At step 52, the method 50 comprises drying an olive leaf extract, beef bone meal, and moringa seed gel at a temperature of 100 to 150° C. for 1 to 5 h to obtain a mixture of olive leaf extract, beef bone meal, and moringa seed gel. In one embodiment, the method comprises drying the olive leaf extract, beef bone meal, and moringa seed gel at a temperature of 102 to 148° C., preferably 104 to 146° C., preferably 106 to 144° C., preferably 108 to 142° C., preferably 110 to 140° C., preferably 112 to 138° C., preferably 114 to 138° C., preferably 116 to 138° C., preferably 118 to 138° C., preferably 120 to 138° C., preferably 122 to 138° C., preferably 124 to 138° C., preferably 126 to 138° C., preferably 128 to 138° C., preferably 130 to 138° C., preferably 132 to 138° C., preferably 134 to 138° C., preferably 136 to 138° C., most preferably 138° C. In one embodiment, the method comprises drying the olive leaf extract, beef bone meal, and moringa seed gel for 1.5 to 4.5 h, preferably 2 to 4 h, preferably 2.5 to 3.5 h, preferably 3 to 3.5 h, most preferably 3.5 h. The drying can be performed in any suitable method known in the art. In a preferred embodiment, the drying is completed in an oven. In a specific embodiment, the olive leaf extract, beef bone meal, and moringa seed gel are heated in an oven at 138° C. for about 3 to 4 hours, preferably for about 3.5 hours, to obtain the mixture. In one embodiment, after drying, the mixture of olive leaf extract, beef bone meal, and moringa seed gel is ground to obtain an average particle size of 50 nm or less, preferably 49 nm or less, preferably 48 nm or less, preferably 47 nm or less, preferably 46 nm or less, preferably 45 nm or less, preferably 44 nm or less, preferably 43 nm or less, preferably 42 nm or less, preferably 41 nm or less, preferably 40 nm or less, preferably 39 nm or less, preferably 38 nm or less, preferably 37 nm or less, preferably 36 nm or less, preferably 35 nm or less, preferably 34 nm or less, preferably 33 nm or less, preferably 32 nm or less, preferably 31 nm or less, most preferably 30 nm or less.

At step 54, the method 50 comprises hydrolyzing the mixture of olive leaf extract, beef bone meal, and moringa seed gel with at least one inorganic acid to obtain the nanocomposite. In some embodiments, the inorganic acid may include, but are not limited to, sulfuric acid ($H_2SO_4$), nitric acid ($HNO_3$), phosphoric acid ($H_3PO_4$), hydrofluoric acid (HF), trifluoroacetic acid, perchloric acid ($HClO_4$), hydrobromic acid (HBr), hydroiodic acid (HI), chromic acid ($H_2CrO_4$), boric acid ($H_3BO_3$), periodic acid ($HIO_4$), selenic acid ($H_2SeO_4$), telluric acid ($H_6TeO_6$), sulfurous acid ($H_2SO_3$), nitrous acid ($HNO_2$), hypochlorous acid (HClO), chloric acid ($HClO_3$), iodic acid ($HIO_3$), bromic acid ($HBrO_3$), fluorosilicic acid ($H_2SiF_6$), carbonic acid ($H_2CO_3$), arsenic acid ($H_3AsO_4$), antimonic acid ($HSbO_3$), tungstic acid ($H_2WO_4$), vanadic acid ($H_3VO_4$), manganic acid ($H_2MnO_4$), pyrophosphoric acid ($H_4P_2O_7$), metaphosphoric acid ($HPO_3$), formic acid (HCOOH), and acetic acid ($CH_3COOH$). In a preferred embodiment, the inorganic acid is at least one selected from the group consisting of HCl and $H_2SO_4$. In some embodiments, the inorganic acid is HCl. In one embodiment, the HCl has a concentration of 80 to 90%. In some embodiments, the concentration of HCl is 81%, 82%, 83%, 84%, 85%, 86%, 87%, 88%, 89%, or 90%. In a preferred embodiment, the concentration of HCl is 88%. In some embodiments, the inorganic acid is sulfuric acid. In one embodiment, the sulfuric acid has a concentration of 90 to 95%. In some embodiments, the concentration of sulfuric acid is 91%, 92%, 93%, 94%, or 95%. In a preferred embodiment, the concentration of sulfuric acid is 92%. In an embodiment, each component of the mixture is hydrolyzed individually to obtain their respective nanoparticles. In a preferred embodiment, the HCl concentration used to hydrolyze moringa seed coat is about 86%. In a preferred embodiment, the HCl concentration used to hydrolyze olive leaves is about 86%. In a preferred embodiment, the $H_2SO_4$ concentration used to hydrolyze beef bone meal is about 92%.

At step 56, the method 50 comprises preparing ZnO nanoparticles. The ZnO nanoparticles are prepared by reacting a zinc precursor with an organic solvent to obtain a reaction mixture. In one embodiment, the zinc precursor may be selected from a zinc citrate, a zinc iodide, zinc perchlorate, zinc phosphate, zinc triflate, zinc bis(trifluoromethanesulfonyl)imide, zinc tetrafluoroborate, zinc bromide, a hydrate thereof, or mixtures thereof. In alternate embodiments, the zinc precursor is selected from a zinc nitrate hydrate, a zinc chloride hydrate, a zinc sulfate hydrate, and a zinc acetate hydrate. Preferably, the zinc precursor is in a nitrate form because the nitrate form has greater water solubility, thereby achieving greater homogenization during synthesis of the reaction mixture. In a preferred embodiment, the zinc precursor is zinc nitrate hexahydrate ($Zn(NO_3)_2 \cdot 6H_2O$). In some embodiments, the zinc precursor is mixed with the organic solvent to obtain the reaction mixture. Suitable examples of organic solvents include ethanol, methanol, and other polar organic solvents. In an embodiment, the organic solvent is at least one selected from the group consisting of ethanol, methanol, and propanol. The reaction mixture is then heated to a temperature of at least 100° C. to obtain a final suspension. In some embodiments, the reaction mixture is heated to a temperature of 101° C., preferably 102° C., preferably 103° C., preferably 104° C., preferably 105° C., preferably 106° C., preferably 107° C., preferably 108° C., preferably 109° C., preferably 110° C., preferably 111° C., preferably 112° C., preferably 113° C., preferably 114° C., preferably 115° C., preferably 116° C., preferably 117° C., preferably 118° C., preferably 119° C., most preferably 120° C. In a preferred embodiment, the reaction mixture is heated to a temperature of 120° C. to obtain a final suspension. The heating can be done by using heating appliances such as hot plates, muffle furnace, tube furnace, heating mantles ovens, microwaves, autoclaves, tapes, oil baths, salt baths, sand baths, air baths, hot-tube furnaces, hot-air guns, and other methods known in the art. In some embodiments, the final suspension is then centrifuged to separate the ZnO nanoparticles from the reaction medium and unreacted precursors. In an embodiment, the final suspension is centrifuged at 1,000 to 8,000 rpm for 1 to 30 min to obtain the ZnO nanoparticles. In one embodiment, the final suspension is centrifuged at 1,500 to 7,500 rpm, preferably 2,000 to 7,000 rpm, preferably 2,500 to 6,500 rpm, preferably 3,000 to 6,000 rpm, preferably 3,000 to 5,500 rpm, preferably 3,000 to 5,000 rpm, preferably 3,000 to 4,500 rpm, preferably 3,000 to 4,000 rpm, preferably 3,000 to 3,500 rpm, most preferably 3,000 rpm. In another embodiment, the final suspension is centrifuged for 2 to 30 min, preferably 3 to 30 min, preferably 4 to 30 min, preferably 5 to 30 min, preferably 6 to 30 min, preferably 7 to 30 min, preferably 8 to 30 min, preferably 9 to 30 min, preferably 10 to 30 min, preferably 11 to 30 min, preferably 12 to 30 min, preferably 13 to 30 min, preferably 14 to 30 min, preferably 15 to 30 min, preferably 16 to 30 min, preferably 17 to 30 min, preferably 18 to 30 min, preferably 19 to 30 min, preferably 20 to 30 min, preferably 21 to 30 min, preferably 22 to 30 min, preferably 23 to 30 min, preferably 24 to 30 min, preferably 25 to 30 min, preferably 26 to 30 min, preferably 27 to 30 min, preferably 28 to 30 min, preferably 29 to 30 min, most preferably 30 min. In a preferred embodiment, the final suspension is centrifuged at 3,000 rpm for 30 min.

Figure 2A:
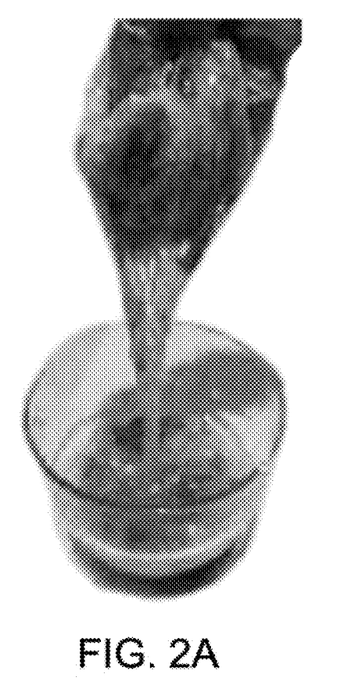
FIG. 2A is an optical image of an okra gel, according to certain embodiments.
Figure 2B:
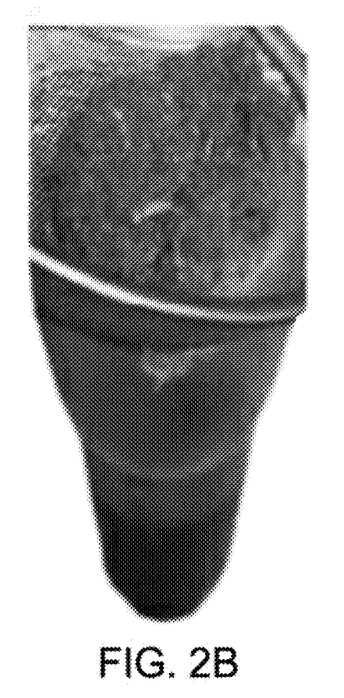
FIG. 2B is an optical image of an olive leaf extract, according to certain embodiments.
Figure 2C:
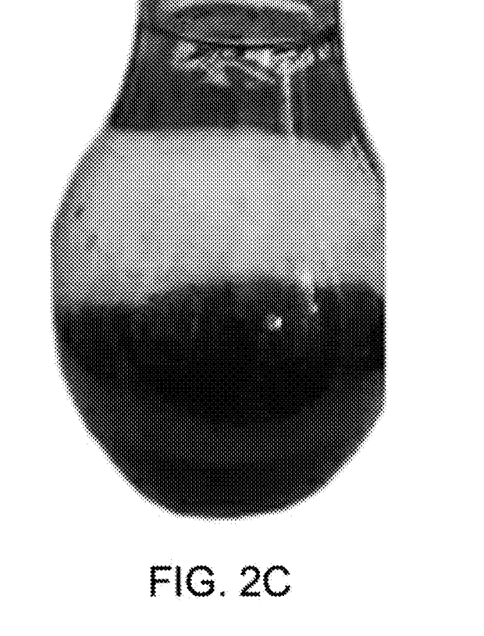
FIG. 2C is an optical image showing acid hydrolysis of the olive leaf extract, according to certain embodiments.
Figure 2D:
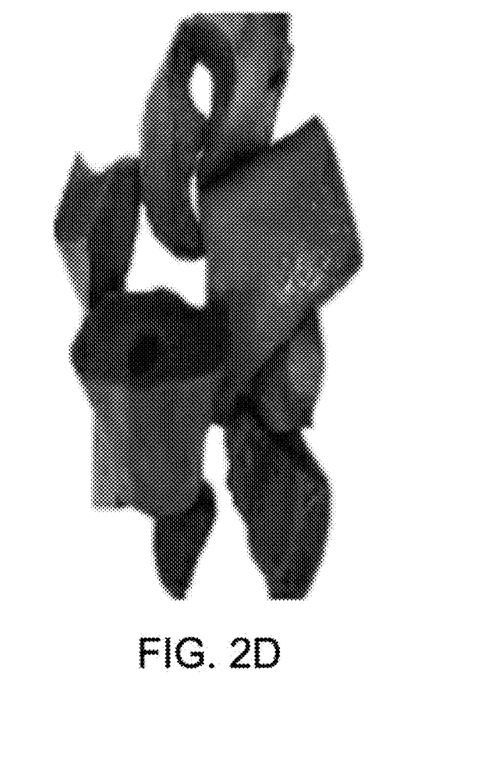
FIG. 2D is an optical image of a beef bone, according to certain embodiments.
Figure 2E:
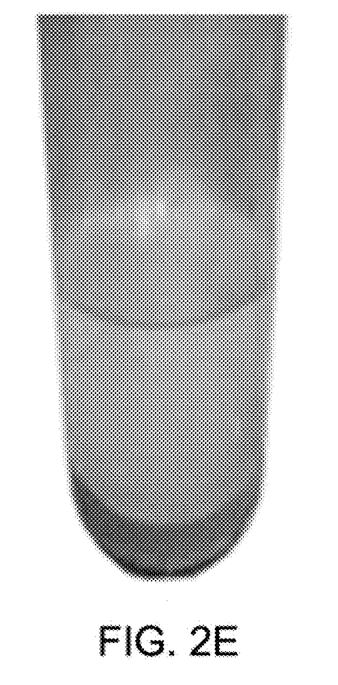
FIG. 2E is an optical image of the beef bone, and a solution obtained on acid hydrolysis of the beef bone, according to certain embodiments.
Figure 2F:
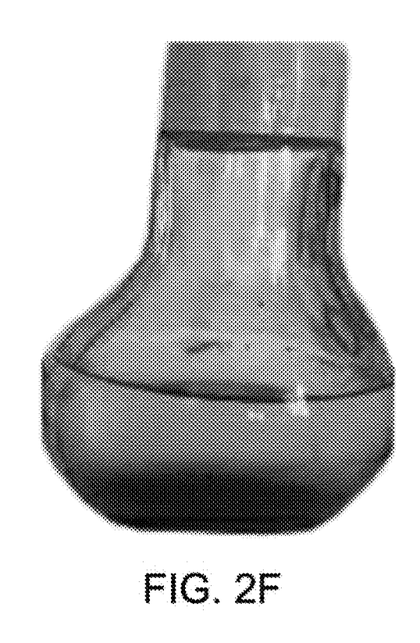
FIG. 2F is an optical image of a solution obtained on acid hydrolysis of moringa nanoparticles, according to certain embodiments.
Figure 2G:
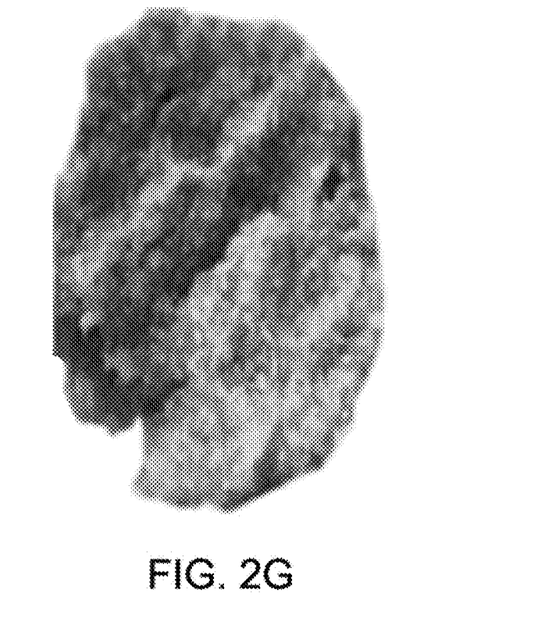
FIG. 2G is an optical image of moringa seed gel, according to certain embodiments.
Figure 2H:
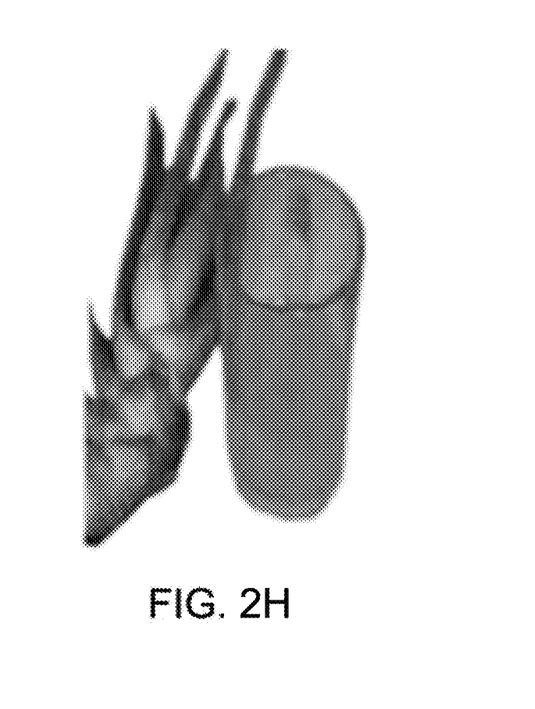
FIG. 2H is an optical image of aloe vera gel, according to certain embodiments.
Figure 2I:
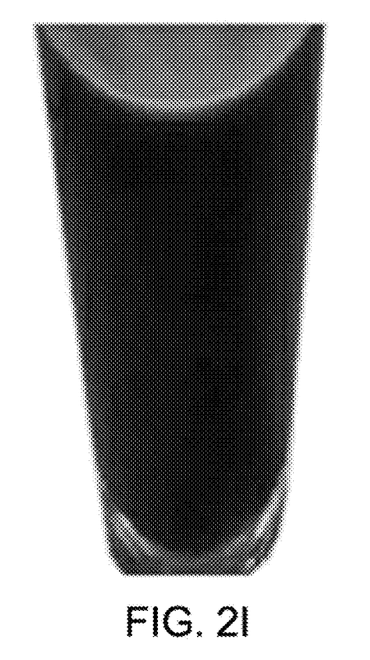
FIG. 2I is an optical image of a pomegranate peel dye, according to certain embodiments.
Figure 2J:
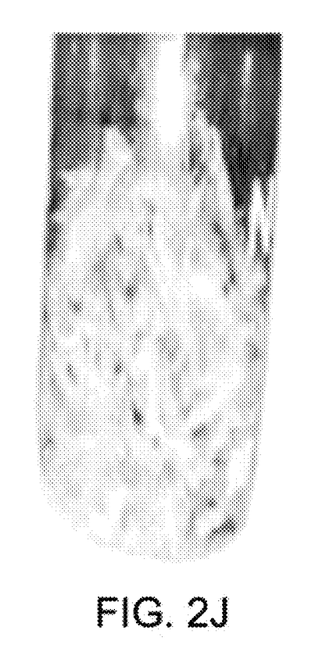
FIG. 2J is an optical image of a chicken leg, according to certain embodiments.
Figure 2K:
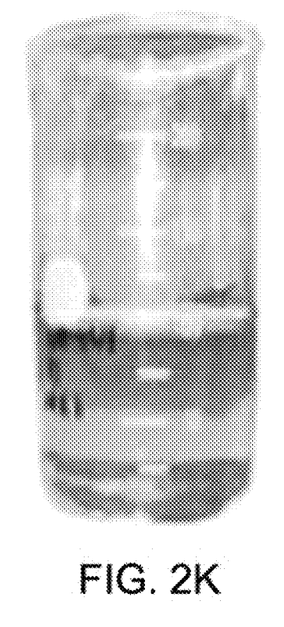
FIG. 2K is an optical image of a glycerin solution, according to certain embodiments.
Figure 2L:
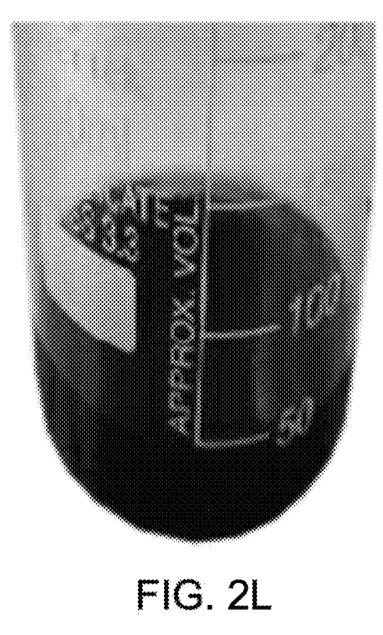
FIG. 2L is an optical image of a black seed extract, according to certain embodiments.
Figure 2M:
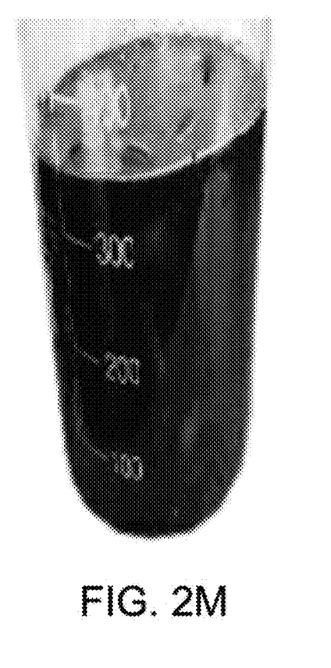
FIG. 2M is an optical image of a beetroot dye, according to certain embodiments.
Figure 2N:
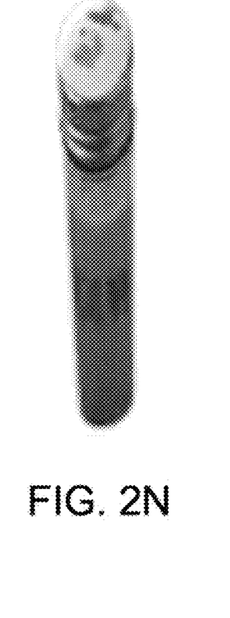
FIG. 2N is an optical image of the biobased wound healing preparation, according to certain embodiments.

At step 58, the method 50 comprises combining the nanocomposite with the organic composition, ZnO nanoparticles, and the adhesive component to form the biobased wound healing preparation. Pictorial representations of each component used in the biobased wound healing preparation are described in FIG. 2A through FIG. 2N.

Figure 2O:
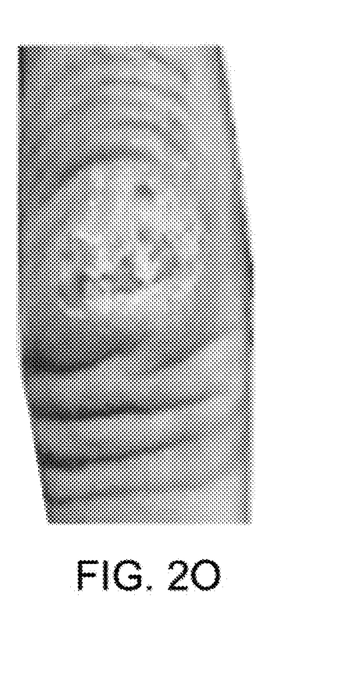
FIG. 2O is an optical image of a wound, according to certain embodiments.
Figure 2P:
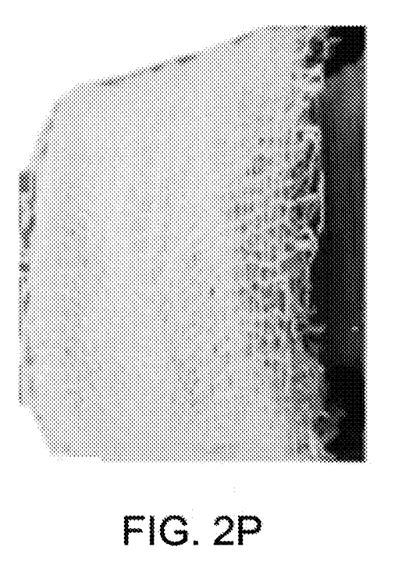
FIG. 2P is an optical image of the wound covered with the biobased wound healing preparation, according to certain embodiments.
Figure 2Q:
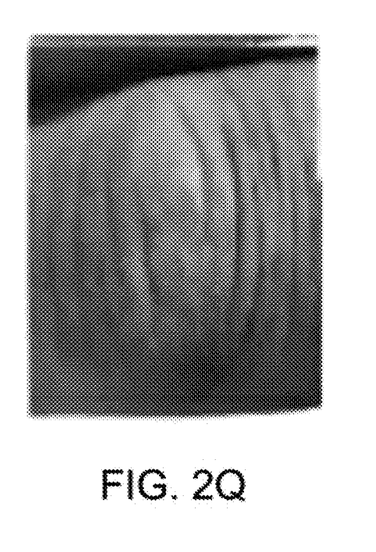
FIG. 2Q is an optical image depicting wound recovery using the biobased wound healing preparation, according to certain embodiments.

In an embodiment, the biobased wound healing preparation can be used to repair a wound. In some embodiments, the wound may be at least one selected from the group consisting of a burn, a blister, a scrape, an abrasion, a puncture, a laceration, an incision, an ulcer, a surgical wound, a pressure sore, a diabetic wound, a contusion, a sprain, a strain, a bruise, a stab wound, a bite wound, a gunshot wound, a gunpowder burn, a frostbite, a chemical burn, a thermal burn, a radiation burn, a poison ivy rash, a sunburn, a corneal abrasion, a venous ulcer, an arterial ulcer, a chronic wound, and a post-surgical wound. In a preferred embodiment, the wound is at least one selected from a cut, a tear, and a fracture. The optical images of the wound, the wound covered with the biobased wound healing preparation, and its recovery with the biobased wound healing preparation of the present disclosure are depicted in FIG. 2O through FIG. 2Q respectively.

EXAMPLES

The following examples illustrate a biobased wound healing preparation. The examples are provided solely for illustration and are not to be construed as limitations of the present disclosure, as many variations thereof are possible without departing from the spirit and scope of the present disclosure.

Example 1: Materials

The olive leaf extract was obtained by grinding olive leaves in a blender then using a mortar and pestle and an extraction sieve. The beef bone meal was obtained by crushing beef bone and hydrolyzing the crushed beef bone with acid. The moringa seed gel was prepared by soaking moringa seeds in the water then using a mortar and pestle to form a glue. The glue was then prepared into a suspension and heated to form the gel. Beetroot peel dye was obtained by grinding beetroot peels in a blender then using a mortar and pestle to obtain a fine powder of the peels. 70% ethanol was then used to extract the beetroot peel dye from the powder. The black cumin seed was prepared by extraction with 70% ethanol to obtain a black cumin seed pigment. The chicken-sourced glycerin was prepared by a transesterification process using a shaker at 60° C. Finally, the pomegranate pigment was prepared by 70% ethanol extraction, then the extracted pigment was heated with 30% water to obtain the final pomegranate pigment.

Example 2: pH, Antioxidant, Cellulose, and Starch Determination

The pH, antioxidant, cellulose, and starch of the biobased wound healing preparation of the present disclosure were determined, and their values were compared to synthetic wound healing materials available in the market. The quantitative determination of pH, antioxidant, cellulose, and starch was carried out using methods known in the art. The results of this study are depicted in Table 1.

TABLE 1 pH, antioxidant, cellulose, and starch determination

| Materials | pH determination | Cellulose determination | Starch determination |
|---|---|---|---|
| Biobased wound healing preparation | 7.5 ± 0.03 | 38.3% ± 0.01 | 30.0% ± 0.01 |
| Synthetic wound healing materials | Alkaline ≥7 | It is zero if from gas or oil; if from starch sample, it is 20-40%. | It is zero if from gas or oil, if from starch sample it is 10-30%. |

Mean ± SE (standard Error, n = 3)

Example 3: Nanostarch Measurement

The particle size of the nanostarch was measured by Scanning Electron Microscopy (SEM), and the results indicate that the average nanoparticle size of the biobased wound healing preparation was 15 nm. Preparations comprising nanoparticles may aid wound healing in comparison to preparations comprising larger particle sizes due to nanoparticles' high surface area, which may help promote cell proliferation, angiogenesis, and reduce inflammation.

TABLE 2

Measurement of nanostarch by SEM

| Materials | Nanostarch size | Nanocellulose size | Average size of the nanoparticle |
|---|---|---|---|
| Biobased wound healing preparation | 14 nm | 16 nm | 15 nm |
| Synthetic wound healing materials | 1-100 nm (standard) | 1-100 nm (standard) | 1-100 nm (standard) |

Example 4: Odor Test

The biobased wound healing preparation was burned using a gas burner. The odor was observed visually and compared with the synthetic dental crown by ASTM D3801. The results of this study are depicted in Table 3.

TABLE 3

Odor test according to the ASTM D3801

| Materials | Moisture percent | Odor |
|---|---|---|
| Biobased wound healing preparation | 27% | Low odor |
| Synthetic wound healing materials | Maximum 30% | Low odor |

Example 5: Chemical Element Test

Chemical element tests, such as Na, K, $CO_3^-$, Cl, Ca, Si, Fe, Pb, Cu, Al, Sn, and Zn, were determined using the EN (166) [European Norm, 166] standardization. Similar results were exhibited when compared to synthetic wound healing materials. All the elements showed values under the standard. The results of this study are depicted in Table 4.

TABLE 4

Determination of Chemical Element Test by EN (European Standard EN166)

| Chemical Elements (ppm) | Biobased wound healing preparation | Synthetic wound healing materials |
|---|---|---|
| K | 8.0 ± 0.4b | 10 |
| Na | 4.1 ± 0.3bc | 5 |
| Cl | 0.58 ± 0.02d | 2 |
| CO3— | 155 ± 1.0a | 440-5 |
| Ca | 10.0 ± 0.02a | 10 |
| Si | 3.5 | 5 |
| Fe | 1.9 | 5 |
| Pb | 0 | 5 |
| Cu | 0.33 | 5 |
| Al | 1.3 | 5 |
| Sn | 1.5 | 5 |
| Zn | 3.5 | 5 |

Mean ± standard error (SE, n = 3). Different letters mean the significant difference at a 5% level of significance by LSD test.

Example 6: Wound Healing Timing

The effects of the biobased wound healing preparation and the synthetic wound healing materials on wound healing were studied, and the results of this study are depicted in Table 5. Table 5. Effects of biobased wound healing preparations on wound healing. The bio-based would healing preparation was applied to a patient's wound located on the finger. A total of three patients were utilized for the study. The bio-based wound healing preparation was applied to the wounds once a day for 10 days at a dose of 0.25 mL (5 drops). Patients from Imam Mohammad Saud Islamic University Medical Center were utilized for this study. The bio-based wound healing preparation was compared to a combination of synthetic wound healing materials comprising 70% of Fusidate H 10 g and 30% salicylic acid ointment 30 g.

| Samples | Days recovered | Percentage recovery |
|---|---|---|
| Biobased wound healing preparation | 10 ± 0.2 | 90 |
| Synthetic wound healing materials | 7 ± 0.1 | 99 |

Mean ± standard error (SE, n = 3).

Numerous modifications and variations of the present disclosure are possible in light of the above teachings. It is, therefore, to be understood that within the scope of the appended claims, the invention may be practiced otherwise than as specifically described herein.

The invention claimed is:

1. A biobased wound healing preparation, comprising:
   a nanocomposite comprising olive leaf extract, beef bone meal, and moringa seed gel;
   an organic composition comprising at least one selected from the group consisting of a beetroot dye, black cumin seed, sodium fusidate, salicylic acid, chicken-sourced glycerin, and pomegranate peel pigment;
   an adhesive component comprising at least one of a cyanoacrylate, *Acacia nilotica* glue, coconut gel, okra gel, aloe vera gel, and aroid root gum; and
   ZnO nanoparticles,
   wherein the nanocomposite is in the form of nanoparticles having an average particle size of 25 nm or less.

2. The biobased wound healing preparation of claim 1, wherein the organic composition comprises 1 to 5 wt. % of at least one selected from the group consisting of fusidic acid and salicylic acid relative to a total weight of the organic composition.

3. The biobased wound healing preparation of claim 1, wherein the biobased wound healing preparation comprises ZnO nanoparticles in an amount of 1 to 10 wt. % relative to a total weight of the biobased wound healing preparation.

4. The biobased wound healing preparation of claim 1, wherein the nanocomposite is a cellulose composition comprising 25 to 50 wt. % of a nanocellulose relative to a total weight of the nanocomposite.

5. The biobased wound healing preparation of claim 1, wherein the nanocomposite is a starch composition comprising 20 to 40 wt. % of a nanostarch relative to a total weight of the nanocomposite.

6. The biobased wound healing preparation of claim 1, wherein the nanocomposite is in the form of nanoparticles having an average particle size of 15 nm or less.

7. The biobased wound healing preparation of claim 1, wherein the biobased wound healing preparation comprises ZnO nanoparticles in an amount of 1 to 5 wt. % relative to a total weight of the biobased wound healing preparation.

8. The biobased wound healing preparation of claim 1, wherein the biobased wound healing preparation achieves a wound healing time of less than 8 days as compared to a synthetic polymer wound healing preparation.

9. The biobased wound healing preparation of claim 1, wherein the biobased wound healing preparation comprises the nanocomposite in an amount of 35 to 55 wt. % relative to a total weight of the biobased wound healing preparation.

10. The biobased wound healing preparation of claim 1, wherein the ZnO nanoparticles are spherical and have an average particle size of 40 nm or less.

11. The biobased wound healing preparation of claim 1, wherein the biobased wound healing preparation has a pH of 5 to 8.

12. A method of producing the biobased wound healing preparation of claim 1, comprising:
    hydrolyzing a mixture of olive leaf extract, beef bone meal, and moringa seed gel with at least one inorganic acid to obtain the nanocomposite;
    preparing ZnO nanoparticles; and
    combining the nanocomposite with the organic composition, ZnO nanoparticles, and the adhesive component to form the biobased wound healing preparation.

13. The method of claim 10, further comprising:
    drying the olive leaf extract, beef bone meal, and moringa seed gel at a temperature of 100 to 150° C. for 1 to 5 h to obtain the mixture of olive leaf extract, beef bone meal, and moringa seed gel.

14. The method of claim 10, wherein the inorganic acid is selected from the group consisting of hydrochloric acid, sulfuric acid, nitric acid, phosphoric acid, hydrofluoric acid, formic acid, and trifluoroacetic acid.

15. The method of claim 10, wherein the preparing comprises reacting a zinc precursor with an organic solvent to obtain a reaction mixture, sonicating the reaction mixture then heating the reaction mixture for 12 to 36 h to obtain a final suspension, and centrifuging the final suspension to obtain the ZnO nanoparticles.

16. The method of claim 10, wherein the inorganic acid is selected from the group consisting of hydrochloric acid and sulfuric acid.

17. The method of claim 10, wherein the ZnO nanoparticles have an average particle size of 40 nm or less.

18. The method of claim 10, wherein the organic composition comprises beetroot dye in an amount of 5 to 15 wt. % relative to a total weight of the organic composition.

19. The method of claim 10, wherein the organic composition comprises pomegranate peel pigment in an amount of 5 to 15 wt. % relative to a total weight of the organic composition.

* * * * *